United States Patent
Nishizaka et al.

(10) Patent No.: US 12,059,594 B2
(45) Date of Patent: Aug. 13, 2024

(54) RUNNING METHOD DETERMINATION DEVICE, RUNNING-METHOD DETERMINATION METHOD, AND PROGRAM

(71) Applicant: CASIO COMPUTER CO., LTD., Tokyo (JP)

(72) Inventors: Nobuyoshi Nishizaka, Tokyo (JP); Futoshi Yamamoto, Hamura (JP); Tsutomu Hiroyama, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 284 days.

(21) Appl. No.: 17/442,781

(22) PCT Filed: Mar. 12, 2020

(86) PCT No.: PCT/JP2020/010732
§ 371 (c)(1),
(2) Date: Sep. 24, 2021

(87) PCT Pub. No.: WO2020/195874
PCT Pub. Date: Oct. 1, 2020

(65) Prior Publication Data
US 2022/0161095 A1    May 26, 2022

(30) Foreign Application Priority Data
Mar. 25, 2019    (JP) .................................. 2019-055911

(51) Int. Cl.
*A63B 24/00*    (2006.01)
*A63B 69/00*    (2006.01)

(52) U.S. Cl.
CPC ...... *A63B 24/0062* (2013.01); *A63B 69/0028* (2013.01); *A63B 2220/44* (2013.01); *A63B 2220/53* (2013.01); *A63B 2220/62* (2013.01); *A63B 2220/803* (2013.01); *A63B 2220/836* (2013.01); *A63B 2225/54* (2013.01)

(58) Field of Classification Search
None
See application file for complete search history.

(56) References Cited

U.S. PATENT DOCUMENTS

| | | | |
|---|---|---|---|
| 8,712,508 B2 | 4/2014 | Izumida et al. | |
| 11,016,111 B1* | 5/2021 | Chuang | A61B 5/6807 |
| 2009/0047645 A1* | 2/2009 | Dibenedetto | A61B 5/0002 |
| | | | 434/258 |

(Continued)

FOREIGN PATENT DOCUMENTS

| | | |
|---|---|---|
| CN | 103308068 A | 9/2013 |
| JP | 2012228568 A | 11/2012 |

(Continued)

OTHER PUBLICATIONS

Japanese Office Action (and English language translation thereof) dated Dec. 14, 2021, issued in counterpart Japanese Application No. 2019-055911.

(Continued)

*Primary Examiner* — Sunit Pandya
(74) *Attorney, Agent, or Firm* — Holtz, Holtz & Volek PC

(57) ABSTRACT

A running method determination device includes at least one processor that executes a program stored in at least one memory. The at least one processor acquires motion data at a time of running of a user, calculates, based on acceleration data in multiple axial directions included in the acquired motion data, a sum of acceleration vectors in the multiple axial directions as a resultant vector, and determines a type of a running method of the user using at least an angle of the calculated resultant vector as a standard of determination.

15 Claims, 7 Drawing Sheets

(56) References Cited

U.S. PATENT DOCUMENTS

| | | | |
|---|---|---|---|
| 2014/0342329 A1 | 11/2014 | Debenetto et al. | |
| 2016/0030804 A1* | 2/2016 | Mizuochi | A61B 5/11 |
| | | | 482/8 |
| 2016/0030823 A1* | 2/2016 | Sato | G09B 19/0038 |
| | | | 434/255 |
| 2016/0180440 A1 | 6/2016 | Dibenedetto et al. | |
| 2016/0287937 A1 | 10/2016 | Fitzgerald et al. | |
| 2017/0095692 A1 | 4/2017 | Chang et al. | |
| 2018/0007277 A1* | 1/2018 | Aibara | H04N 5/2627 |
| 2018/0366025 A1 | 12/2018 | Dibenedetto et al. | |
| 2018/0373926 A1 | 12/2018 | Mizuochi et al. | |
| 2020/0335006 A1 | 10/2020 | Dibenedetto et al. | |

FOREIGN PATENT DOCUMENTS

| | | | |
|---|---|---|---|
| JP | 2016034479 A | 3/2016 | |
| JP | 2016034482 A | 3/2016 | |
| JP | 6463587 B1 | 1/2019 | |

OTHER PUBLICATIONS

Chinese Office Action (and English language translation thereof) dated Feb. 23, 2022, issued in counterpart Chinese Application No. 202080020538.2.

International Preliminary Report on Patentability (IPRP) (and English language translation thereof) dated Sep. 28, 2021 issued in International Application No. PCT/JP2020/010732.

Extended European Search Report (EESR) dated Apr. 8, 2022, issued in counterpart European Application No. 20778187.3.

Chinese Office Action (and English language translation thereof) dated Aug. 1, 2022, issued in counterpart Chinese Application No. 202080020538.2.

International Search Report (ISR) (and English language translation thereof) dated Jun. 2, 2020, issued in International Application No. PCT/JP2020/010732.

Written Opinion dated Jun. 2, 2020, issued in International Application No. PCT/JP2020/010732.

* cited by examiner

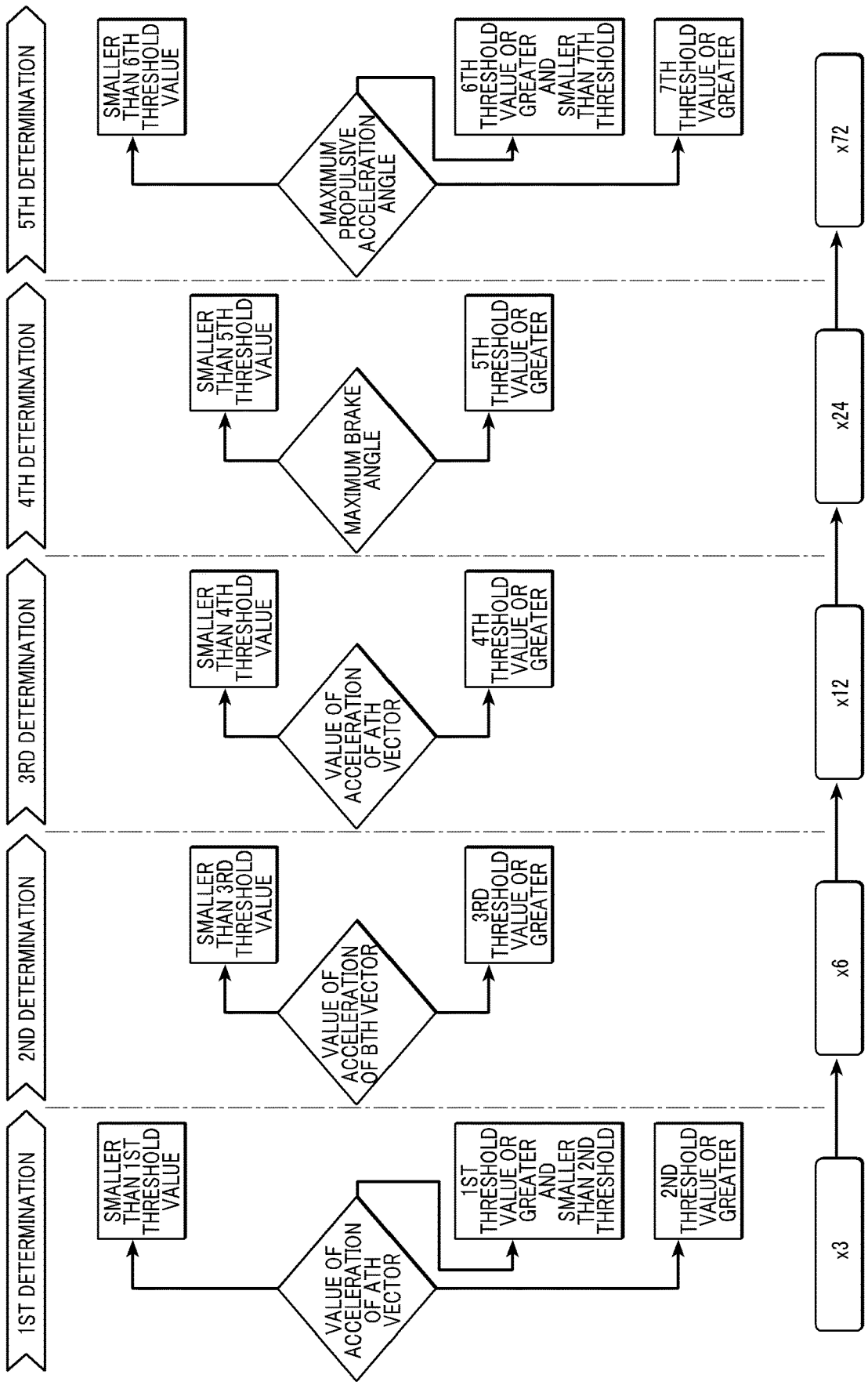

FIG. 6

*1: 6TH THRESHOLD VALUE OR GREATER AND SMALLER THAN 7TH THRESHOLD VALUE

| 1ST DETERMINATION | 2ND DETERMINATION | 3RD DETERMINATION | 4TH DETERMINATION | 5TH DETERMINATION | TYPE IN SECTION OF BRAKING | DETAILED CLASSIFICATION |
|---|---|---|---|---|---|---|
| SMALLER THAN 1ST THRESHOLD VALUE | SMALLER THAN 3RD THRESHOLD VALUE | SMALLER THAN 4TH THRESHOLD VALUE | SMALLER THAN 5TH THRESHOLD VALUE | SMALLER THAN 6TH THRESHOLD VALUE | REVERSE L | REVERSE L 1 |
| | | | | *1 | | REVERSE L 2 |
| | | | | 7TH THRESHOLD VALUE OR GREATER | | REVERSE L 3 |
| | | | 5TH THRESHOLD VALUE OR GREATER | SMALLER THAN 6TH THRESHOLD VALUE | REVERSE L | REVERSE L 4 |
| | | | | *1 | | REVERSE L 5 |
| | | | | 7TH THRESHOLD VALUE OR GREATER | | REVERSE L 6 |
| | | 4TH THRESHOLD VALUE OR GREATER | SMALLER THAN 5TH THRESHOLD VALUE | SMALLER THAN 6TH THRESHOLD VALUE | WIDE V | WIDE V 1 |
| | | | | *1 | | WIDE V 2 |
| | | | | 7TH THRESHOLD VALUE OR GREATER | | WIDE V 3 |
| | | | 5TH THRESHOLD VALUE OR GREATER | SMALLER THAN 6TH THRESHOLD VALUE | WIDE V | WIDE V 4 |
| | | | | *1 | | WIDE V 5 |
| | | | | 7TH THRESHOLD VALUE OR GREATER | | WIDE V 6 |
| | 3RD THRESHOLD VALUE OR GREATER | SMALLER THAN 4TH THRESHOLD VALUE | SMALLER THAN 5TH THRESHOLD VALUE | SMALLER THAN 6TH THRESHOLD VALUE | WIDE V | WIDE V 7 |
| | | | | *1 | | WIDE V 8 |
| | | | | 7TH THRESHOLD VALUE OR GREATER | | WIDE V 9 |
| | | | 5TH THRESHOLD VALUE OR GREATER | SMALLER THAN 6TH THRESHOLD VALUE | GRADUAL INCREASE | GRADUAL INCREASE 1 |
| | | | | *1 | | GRADUAL INCREASE 2 |
| | | | | 7TH THRESHOLD VALUE OR GREATER | | GRADUAL INCREASE 3 |
| | | 4TH THRESHOLD VALUE OR GREATER | SMALLER THAN 5TH THRESHOLD VALUE | SMALLER THAN 6TH THRESHOLD VALUE | SYMMETRICAL V | SYMMETRICAL V 1 |
| | | | | *1 | | SYMMETRICAL V 2 |
| | | | | 7TH THRESHOLD VALUE OR GREATER | | SYMMETRICAL V 3 |
| | | | 5TH THRESHOLD VALUE OR GREATER | SMALLER THAN 6TH THRESHOLD VALUE | TRAPEZOID | TRAPEZOID 1 |
| | | | | *1 | | TRAPEZOID 2 |
| | | | | 7TH THRESHOLD VALUE OR GREATER | | TRAPEZOID 3 |
| 1ST THRESHOLD VALUE OR GREATER AND SMALLER THAN 2ND THRESHOLD | SMALLER THAN 3RD THRESHOLD VALUE | SMALLER THAN 4TH THRESHOLD VALUE | SMALLER THAN 5TH THRESHOLD VALUE | SMALLER THAN 6TH THRESHOLD VALUE | REVERSE L | REVERSE L 7 |
| | | | | *1 | | REVERSE L 8 |
| | | | | 7TH THRESHOLD VALUE OR GREATER | | REVERSE L 9 |
| | | | 5TH THRESHOLD VALUE OR GREATER | SMALLER THAN 6TH THRESHOLD VALUE | REVERSE L | REVERSE L 10 |
| | | | | *1 | | REVERSE L 11 |
| | | | | 7TH THRESHOLD VALUE OR GREATER | | REVERSE L 12 |
| | | 4TH THRESHOLD VALUE OR GREATER | SMALLER THAN 5TH THRESHOLD VALUE | SMALLER THAN 6TH THRESHOLD VALUE | WIDE V | WIDE V 10 |
| | | | | *1 | | WIDE V 11 |
| | | | | 7TH THRESHOLD VALUE OR GREATER | | WIDE V 12 |
| | | | 5TH THRESHOLD VALUE OR GREATER | SMALLER THAN 6TH THRESHOLD VALUE | WIDE V | WIDE V 13 |
| | | | | *1 | | WIDE V 14 |
| | | | | 7TH THRESHOLD VALUE OR GREATER | | WIDE V 15 |
| | 3RD THRESHOLD VALUE OR GREATER | SMALLER THAN 4TH THRESHOLD VALUE | SMALLER THAN 5TH THRESHOLD VALUE | SMALLER THAN 6TH THRESHOLD VALUE | WIDE V | WIDE V 16 |
| | | | | *1 | | WIDE V 17 |
| | | | | 7TH THRESHOLD VALUE OR GREATER | | WIDE V 18 |
| | | | 5TH THRESHOLD VALUE OR GREATER | SMALLER THAN 6TH THRESHOLD VALUE | GRADUAL INCREASE | GRADUAL INCREASE 4 |
| | | | | *1 | | GRADUAL INCREASE 5 |
| | | | | 7TH THRESHOLD VALUE OR GREATER | | GRADUAL INCREASE 6 |
| | | 4TH THRESHOLD VALUE OR GREATER | SMALLER THAN 5TH THRESHOLD VALUE | SMALLER THAN 6TH THRESHOLD VALUE | SYMMETRICAL V | SYMMETRICAL V 4 |
| | | | | *1 | | SYMMETRICAL V 5 |
| | | | | 7TH THRESHOLD VALUE OR GREATER | | SYMMETRICAL V 6 |
| | | | 5TH THRESHOLD VALUE OR GREATER | SMALLER THAN 6TH THRESHOLD VALUE | TRAPEZOID | TRAPEZOID 4 |
| | | | | *1 | | TRAPEZOID 5 |
| | | | | 7TH THRESHOLD VALUE OR GREATER | | TRAPEZOID 6 |
| 2ND THRESHOLD VALUE OR GREATER | SMALLER THAN 3RD THRESHOLD VALUE | SMALLER THAN 4TH THRESHOLD VALUE | SMALLER THAN 5TH THRESHOLD VALUE | SMALLER THAN 6TH THRESHOLD VALUE | REVERSE L | REVERSE L 13 |
| | | | | *1 | | REVERSE L 14 |
| | | | | 7TH THRESHOLD VALUE OR GREATER | | REVERSE L 15 |
| | | | 5TH THRESHOLD VALUE OR GREATER | SMALLER THAN 6TH THRESHOLD VALUE | REVERSE L | REVERSE L 16 |
| | | | | *1 | | REVERSE L 17 |
| | | | | 7TH THRESHOLD VALUE OR GREATER | | REVERSE L 18 |
| | | 4TH THRESHOLD VALUE OR GREATER | SMALLER THAN 5TH THRESHOLD VALUE | SMALLER THAN 6TH THRESHOLD VALUE | WIDE V | WIDE V 19 |
| | | | | *1 | | WIDE V 20 |
| | | | | 7TH THRESHOLD VALUE OR GREATER | | WIDE V 21 |
| | | | 5TH THRESHOLD VALUE OR GREATER | SMALLER THAN 6TH THRESHOLD VALUE | WIDE V | WIDE V 22 |
| | | | | *1 | | WIDE V 23 |
| | | | | 7TH THRESHOLD VALUE OR GREATER | | WIDE V 24 |
| | 3RD THRESHOLD VALUE OR GREATER | SMALLER THAN 4TH THRESHOLD VALUE | SMALLER THAN 5TH THRESHOLD VALUE | SMALLER THAN 6TH THRESHOLD VALUE | WIDE V | WIDE V 25 |
| | | | | *1 | | WIDE V 26 |
| | | | | 7TH THRESHOLD VALUE OR GREATER | | WIDE V 27 |
| | | | 5TH THRESHOLD VALUE OR GREATER | SMALLER THAN 6TH THRESHOLD VALUE | GRADUAL INCREASE | GRADUAL INCREASE 7 |
| | | | | *1 | | GRADUAL INCREASE 8 |
| | | | | 7TH THRESHOLD VALUE OR GREATER | | GRADUAL INCREASE 9 |
| | | 4TH THRESHOLD VALUE OR GREATER | SMALLER THAN 5TH THRESHOLD VALUE | SMALLER THAN 6TH THRESHOLD VALUE | SYMMETRICAL V | SYMMETRICAL V 7 |
| | | | | *1 | | SYMMETRICAL V 8 |
| | | | | 7TH THRESHOLD VALUE OR GREATER | | SYMMETRICAL V 9 |
| | | | 5TH THRESHOLD VALUE OR GREATER | SMALLER THAN 6TH THRESHOLD VALUE | TRAPEZOID | TRAPEZOID 7 |
| | | | | *1 | | TRAPEZOID 8 |
| | | | | 7TH THRESHOLD VALUE OR GREATER | | TRAPEZOID 9 |

Running Method Determination Device, Running-Method Determination Method, and Program

CROSS-REFERENCE TO RELATED APPLICATIONS

This application is based upon and claims the benefit of priority from the prior Japanese Patent Application No. 2019-055911, filed on Mar. 25, 2019, the entire contents of which are incorporated herein by reference.

FIELD OF THE INVENTION

The present disclosure relates to a running method determination device, a running-method determination method, and a program that determine running methods.

DESCRIPTION OF THE RELATED ART

Conventionally, there have been disclosed training systems that receive data from a motion monitor measuring performance of a speed, pace, distance, and the like of a runner during running to provide a user with feedback including training information such as whether the user satisfies a specific training standard (for example, see JP 2012-228568 A).

SUMMARY OF INVENTION

Generally, in order to improve the running ability of a user, it is necessary to do efficient training that matches the user's running characteristics.

However, the feedback provided by the training system disclosed in the above-referenced JP 2012-228568 A alone is insufficient as information in view of efficient training for improvement of the running ability.

The present disclosure has been conceived in view of the above-described problems, and has an object of providing a running method determination device, a running-method determination method, and a program that can provide efficient training.

SOLUTION TO PROBLEM

A running method determination device according to the present disclosure includes:
  an acquisition means that acquires motion data at a time of running of a user; and
  a determination means that determines a running method of the user based on the motion data acquired by the acquisition means.

According to the present disclosure, it is possible to provide efficient training for improvement of the user's running ability.

BRIEF DESCRIPTION OF DRAWINGS

FIG. 5 shows steps in determination of a running method.

FIG. 6 is a list showing determined running methods

DETAILED DESCRIPTION OF EMBODIMENTS

Hereinafter, an embodiment of the present invention is described in detail with reference to the attached drawings. The present disclosure is not limited to the illustrated examples.

«Running Method Determination System»

A configuration of this embodiment is described with reference to FIGS. 1 and 2. First, a running method determination system 1 in this embodiment is described with reference to FIG. 1.

Figure 1:
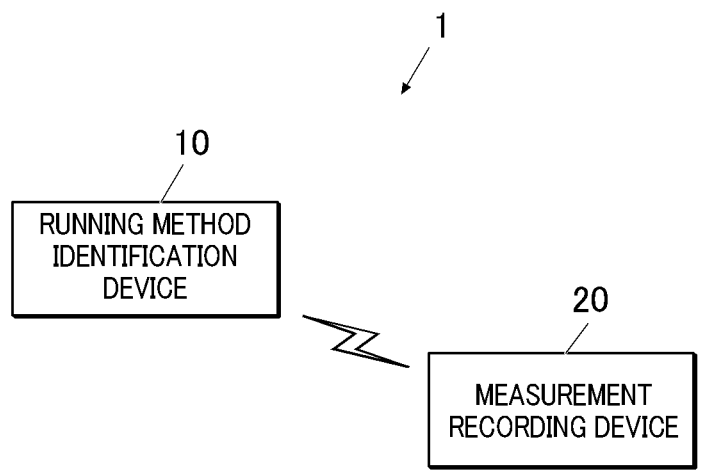
FIG. 1 is a block diagram showing a running style in an embodiment of the present invention.
Figure 2:
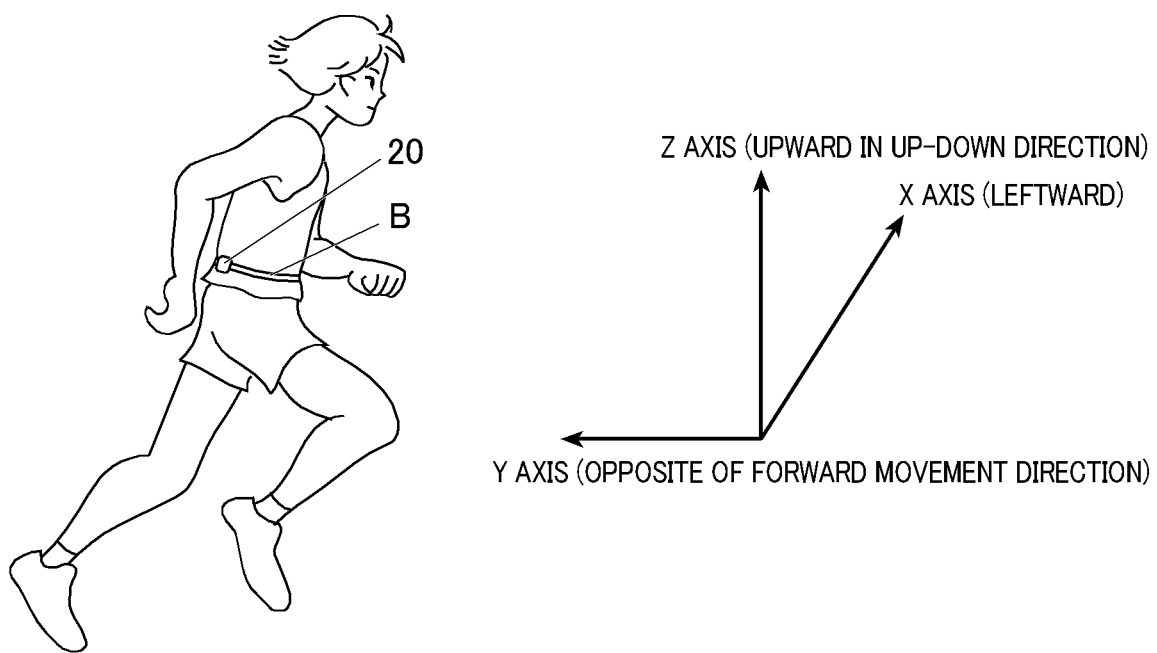
FIG. 2 is an explanatory diagram showing a state where the user wears a measurement recording device.

FIG. 1 is a block diagram showing the running method determination system.

As shown in FIG. 1, the running method determination system 1 includes a running method determination device 10 and a measurement recording device 20.

The running method determination device 10 is a device that determines a running method of a user by using motion data (ex. acceleration data in three axial directions) of the user (measurement target person) acquired from the measurement recording device 20.

The running method determination device 10 is, for example, a smartphone, a laptop PC (personal computer), a desktop PC, a tablet PC, or the like. In the description hereinbelow, the running method determination device 10 is a smartphone.

The measurement recording device 20 is a device that measures and records accelerations in the three axial directions when the user runs. The measurement recording device 20 includes, for example, an accessory belt B, as shown in FIG. 2, and the measurement recording device 20 is fixed at the position of the user's waist with the belt B. Here, the left-right direction is defined as an X-axis, the front-back direction as a Y-axis, and the top-bottom direction as a Z-axis. On the X-axis, the leftward direction is positive and the rightward direction is negative. On the Y-axis, the opposite of the forward movement direction is positive, and the forward movement direction is negative. On the Z axis, the upward direction is positive, and the downward direction is negative.

The measurement recording device 20 may include a clip instead of the belt B, and the measurement recording device 20 may be fixed at the position of the user's waist by fastening the clip to the running clothes.

«Running Method Determination device»

Figure 3A:
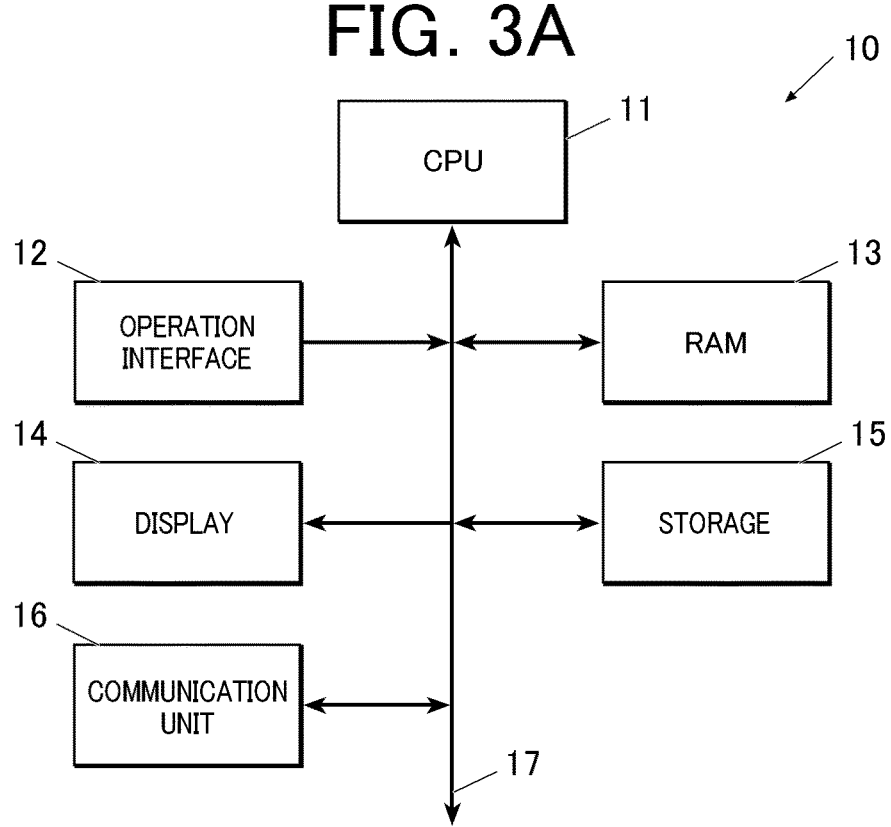
FIG. 3A is a block diagram showing a functional configuration of a running method determination device.

Next, a functional configuration of the running method determination device 10 is described with reference to FIG. 3A. FIG. 3A is a block diagram showing a functional configuration of the running method determination device 10.

The running method determination device 10 includes a central processing unit (CPU) 11, an operation interface 12, a random access memory (RAM) 13, a display 14, a storage 15, and a communication unit 16. The components of the running method determination device 10 are connected to each other by a bus 17.

The CPU (acquisition means, determination means, derivation means) 11 controls the components of the running method determination device 10. The CPU 11 reads a program(s) specified from system programs and application programs stored in the storage 15, deploys the read program(s) in the RAM 13, and performs processing in cooperation with the deployed program(s).

The operation interface 12, which includes a touch panel, for example, receives a touch operation from the user, and outputs the operation information to the CPU 11.

The touch panel is formed integrally with the display 14, and detects the XY coordinates at a contact position on the display 14 by the user by various types of methods of a capacitance method, a resistance film method, and a ultrasonic surface acoustic wave method, for example. The touch panel outputs position signals concerning the XY coordinates of the contact position to the CPU 11.

The RAM 13 is a volatile memory, and forms a work area temporarily storing various kinds of data and programs.

The display 14 includes an LCD (liquid crystal display), an EL (electro luminescence) display, or the like, and displays various screens according to a display information command by the CPU 11.

The storage 15 (storage means) includes, for example, a flash memory, an EEPROM (electrically erasable programmable ROM), an HDD (hard disk drive), and the like. The storage 15 stores a system program(s), an application program(s), data necessary for execution of those programs by the CPU 11, and the like. The storage 15 stores running methods determined by execution of a running method determination process described later (see FIG. 5), motion analysis data (see FIG. 4), and the like.

The communication unit 16 (transmission means) receives the motion data at the time of running training from the measurement recording device 20 or transmits the running methods and the motion analysis data stored in the storage 15 to an external device other than the running method determination device 10 or the measurement recording device 20, and is, for example, a communication unit that uses a wireless communication standard such as Bluetooth (registered trademark) and a wired communication unit such as a USB terminal.

«Measurement Recording Device»

Figure 3B:
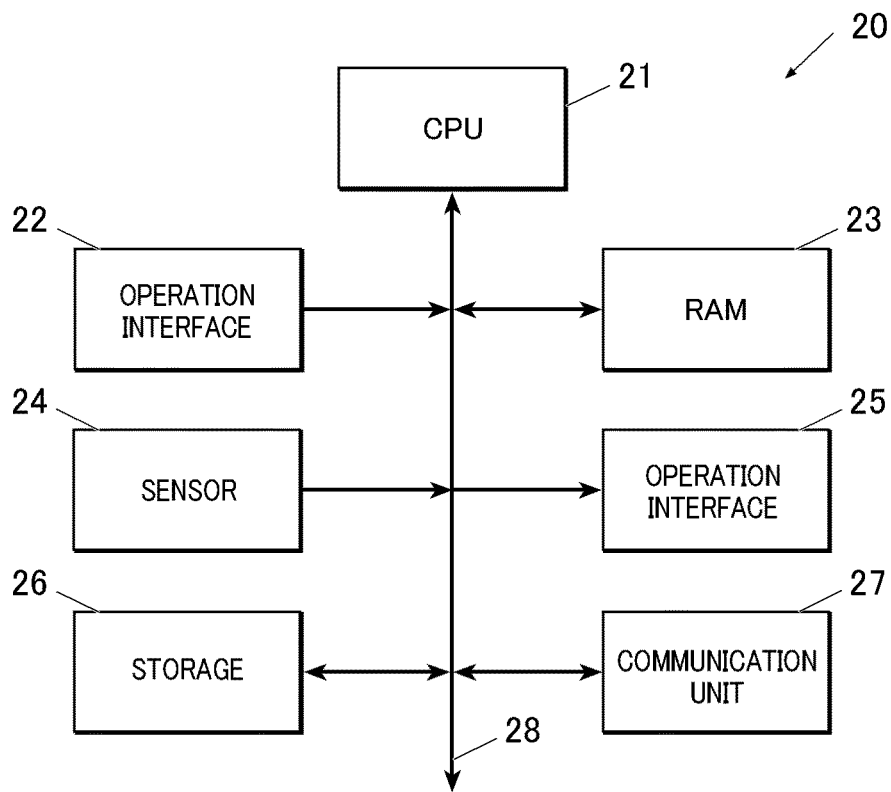
FIG. 3B is a block diagram showing a functional configuration of a measurement recording device.

Next, a functional configuration inside the measurement recording device 20 with reference to FIG. 3B. FIG. 3B is a block diagram showing a functional configuration of the measurement recording device 20.

As shown in FIG. 3B, the measurement recording device 20 includes a CPU 21, an operation interface 22, a RAM 23, a sensor 24, a display 25, a storage 26, and a communication unit 27. The components of the measurement recording device 20 are connected to each other by a bus 28.

The CPU 21 controls the components of the measurement recording device 20. The CPU 21 reads a program(s) specified from system programs and application programs stored in the storage 26, deploys the read program(s) in the RAM 23, and performs processing in cooperation with the deployed program(s).

The operation interface 22 includes a power button (not shown in the drawings) switching the power supply between on and off, a start/stop button (not shown in the drawings) commanding the start and stop of data acquisition, and the like, and the CPU 21 controls the components based on the commands from the operation interface 22.

The RAM 23 is a volatile memory and forms a work area temporarily storing various kinds of data and programs.

The sensor 24 includes a motion sensor that can detect the motion of the measurement recording device 20 such as a three-axis acceleration sensor, a gyro sensor, and a geomagnetic sensor, and a GPS receiver that can acquire the positional information of the measurement recording device 20, and outputs the measurement results to the CPU 21.

The display 25 is a display unit including multiple LED lamps, and can display the state of data transmission (for example, whether data is being transmitted) and the on/off state of the GPS receiver.

The storage 26 includes a flash memory, and an EEPROM. The storage 26 stores a system program(s), an application program(s), data necessary for execution of those programs by the CPU 21, and the like. The storage 26 stores motion data (ex. the acceleration data of the three-axial directions) at the time of running. The acceleration data of the three-axial directions is sampled at a predetermined sampling period (ex. 200 Hz).

The communication unit 27 transmits the motion data at the time of running based on the control of the CPU 21 to the running method determination device 10, and is, for example, a communication unit that uses a wireless communication standard such as Bluetooth (registered trademark) and a wired communication unit such as a USB terminal.

«Running Method Determination Process»

Figure 4:
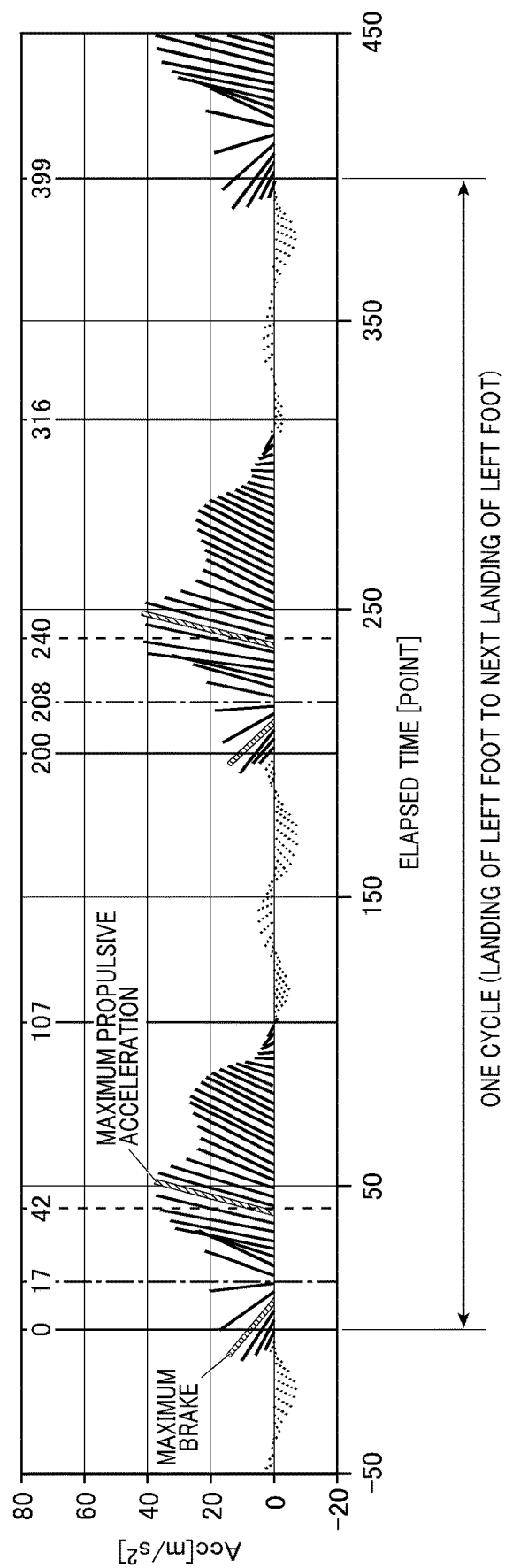
FIG. 4 shows an example of motion analysis data used in determination of a running method.

Next, the running method determination process executed by the running method determination device 10 is described with reference to FIGS. 4 to 7. FIG. 4 is an example of the motion analysis data used in determination of the running method. FIG. 5 shows steps in the determination of the running method. FIG. 6 is a list showing determined running methods. FIGS. 7A to 7E are explanatory diagrams showing characteristics of determined running methods.

The motion analysis data used in the determination of the running methods is described with reference to FIG. 4. The motion analysis data is data derived by the running method determination device 10 based on the motion data (the acceleration of the three-axial directions) acquired from the measurement recording device 20.

The motion analysis data shown in FIG. 4 is motion analysis data at some point at the time of running. In the case where the motion data is continuously acquired by the measurement recording device 20 from the start to the end of running, the running method determination device 10 can derive the motion analysis data at every point from the start to the end of running based on the motion data and thereby determine the running method at every point.

As shown in FIG. 4, on the motion analysis data, the elapsed time is indicated on the horizontal axis, and the resultant vector of the acceleration vector on the Z-axis (see FIG. 2) (in the vertical direction) and the acceleration vector on the Y-axis (see FIG. 2) (in the horizontal direction) are shown at each sampling point of time as an initial point. That is, the variation of the resultant vectors at each elapsed time is shown: the length of the line of the resultant vector (the value of the acceleration of the resultant vector) indicates the magnitude of the acceleration; if the inclination of the line of the resultant vector (the angle of the resultant vector) is in the opposite direction of time elapse from the sampling point of time as the initial point, it indicates that the concerning acceleration serves as a brake on running; and if the inclination of the line of the resultant vector (the angle of the resultant vector) is in the forward direction of time elapse from the sampling point of time as the initial point, it indicates that the concerning acceleration serves as a propulsion on running. The angle of the resultant vector is an angle formed by the radius (ray) extending leftward on the horizontal axis from the sampling point of time of the concerning resultant vector as the initial point rotating to overlap the concerning resultant vector (rotation angle). Here, regarding the elapsed time on the horizontal axis, the period of one cycle since one foot (ex. left foot) touches the ground until that one foot touches the ground the next time is converted (normalized) to 400 points. The start point of a running cycle is defined as a sampling point "0" and the end point of the running cycle as a sampling point "399."

The running method determination in the present disclosure is based on the value of the acceleration of the resultant vector or the angle of the resultant vector at a specific timing in two stage sections of braking and propulsion defined by dividing a running cycle of one foot (ex. left foot) on the above-referenced motion analysis data.

Next, the running method determination process in the present disclosure is described with reference to FIG. 5.

As shown in FIG. 5, as the first determination, the running method determination device 10 first determines whether the value of the acceleration of the Ath (ex. second) resultant vector in the section of braking in one running cycle of one foot (ex. left foot) in the above-described motion analysis data is smaller than the first threshold value (ex. 13 m/s2), equal to or greater than the first threshold value, smaller than the second threshold value (ex. 17 m/s2) or equal to or greater than the second threshold value. Here, for example, the second resultant vector is the resultant vector at the sampling point "1" in FIG. 4. In this first determination, the running method determination is based on the value of the acceleration of the resultant vector at a timing when the Ath (ex. second) resultant vector in the section of braking in one running cycle of one foot (ex. left foot) is calculated.

Subsequently, as the second determination, the running method determination device 10 determines whether the angle of the Bth (ex. fifth) resultant vector in the section of braking in one running cycle of one foot (ex. left foot) in the above-described motion analysis data is smaller than the third threshold value (ex. 45°) or equal to or greater than the third threshold value. Here, for example, the fifth resultant vector is the resultant vector at the sampling point "4" in FIG. 4.

Further, as the third determination, the running method determination device 10 determines whether the value of the acceleration of the Bth (ex. fifth) resultant vector in the section of braking in one running cycle of one foot (ex. left foot) in the above-described motion analysis data is smaller than the fourth threshold value (ex. 30 m/s2), or equal to or greater than the fourth threshold value. In the second to third determinations above, the running method determination is based on the angle of the value of the acceleration of the resultant vector and the angle of the resultant vector at a timing when the Bth (ex. 5th) resultant vector in the section of braking in one running cycle of one foot (ex. left foot).

Subsequently, as the fourth determination, the running method determination device 10 determines whether the angle of the resultant vector of the maximum brake in the section of braking in one running cycle of one foot (ex. left foot) in the above-described motion analysis data is smaller than the fifth threshold value (ex. 60°) or equal to or greater than the fifth threshold value. Here, the resultant vector of the maximum brake is the resultant vector with the maximum acceleration among the resultant vectors that serve as brakes. In the fourth determination, the running method determination is based on the angle of the resultant vector at a timing when the resultant vector with the maximum resultant vector in the section of braking in one cycle of one foot (ex. left foot) is calculated.

Subsequently, as the fifth determination, the running method determination device 10 determines whether the angle of the resultant vector of the maximum propulsive acceleration in the section of propulsion in one running cycle of one foot (ex. left foot) in the above-described motion analysis data is smaller than the sixth threshold value (ex. 100°), equal to or greater than the fifth threshold value, smaller than the seventh threshold value (ex. 110°), or equal to or greater than the seventh threshold value (ex. 110°)." Here, the resultant vector of the maximum propulsive acceleration is the resultant vector with the maximum acceleration among the resultant vectors that serve as propulsive forces.

In this fifth determination, the running method determination is based on the angle of the resultant vector at a timing when the resultant vector with the maximum resultant vector in the section of propulsion in one running cycle of one foot (ex. left foot) is calculated.

As a result, as shown in FIG. 6, the running method determination device 10 determines one pattern from three patterns in the first determination, determines one pattern from two patterns each in the second determination, the three determination, and the fourth determination, determines one pattern from three patterns in the fifth determination, and thereby can determine the running method as one type in the section of braking from five types of reverse-L/wide-V/gradual increase/symmetrical-V/trapezoid, and also as one from detailed classifications (reverse-L 1 to 18 for the reverse-L type, wide-V 1 to 27 for the wide-V type, gradual increase 1 to 9 for the gradual increase type, symmetrical-V 1 to 9 for the symmetrical-V type, trapezoid 1 to 9 for the trapezoid type).

Figure 7A:
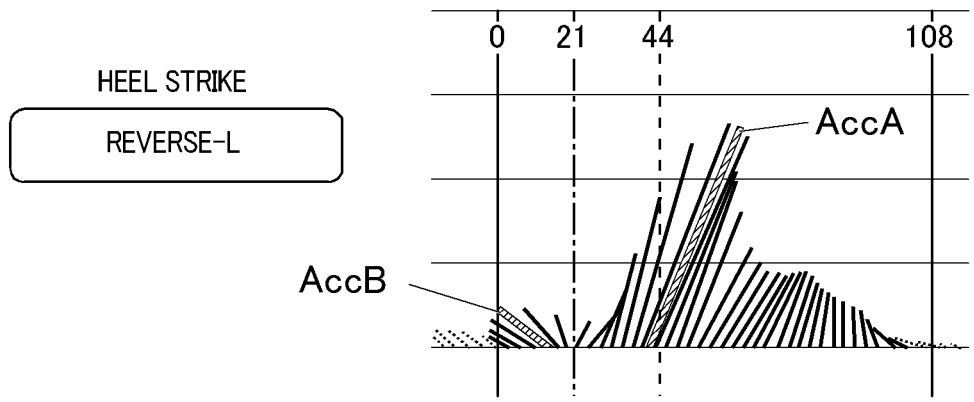
FIG. 7A is an explanatory diagram showing characteristics of a determined running method.

Here, as shown in FIG. 7A, the reverse-L type is a running method with a shape formed by the resultant vector AccA of the maximum propulsive acceleration and the resultant vector AccB of the maximum brake being a reverse-L shape. The reverse-L type is classified into a heel-strike running method characterized in that the foot touches the ground from the heel.

Figure 7B:
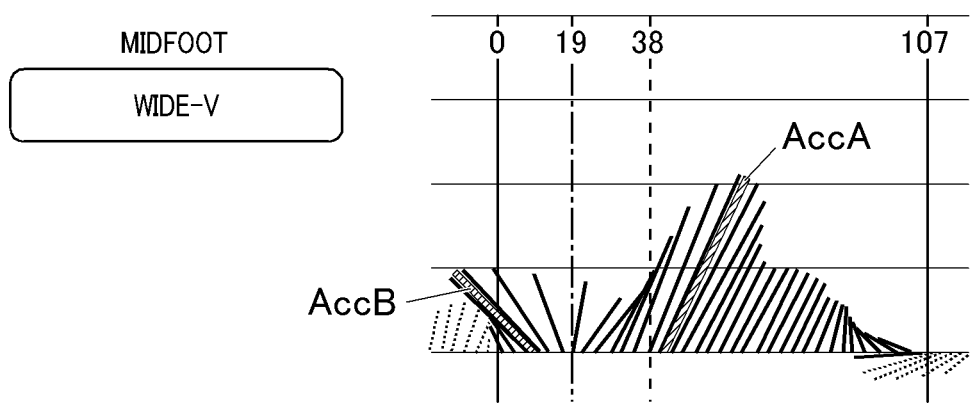
FIG. 7B is an explanatory diagram showing characteristics of a determined running method.

As shown in FIG. 7B, the wide-V type is a running method with a shape formed by the resultant vector AccA of the maximum propulsive acceleration and the resultant vector AccB of the maximum brake being a V-shape wide to the left and right. The wide-V type is classified into a midfoot running method characterized in that the foot touches the ground in a horizontal state.

Figure 7C:
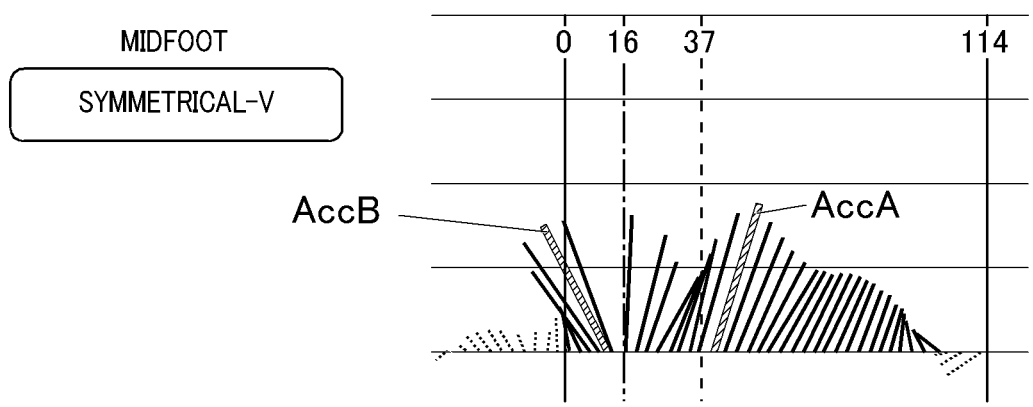
FIG. 7C is an explanatory diagram showing characteristics of a determined running method.

As shown in FIG. 7C, the symmetrical-V type is a running method with a shape formed by the resultant vector AccA of the maximum propulsive acceleration and the resultant vector AccB of the maximum brake being a V-shape symmetrically wide to the left and right. The symmetrical-V type is classified into a midfoot running method similarly to the wide-V type, but may be classified into a midfoot running method closer to a forefoot running method as a detailed classification.

Figure 7D:
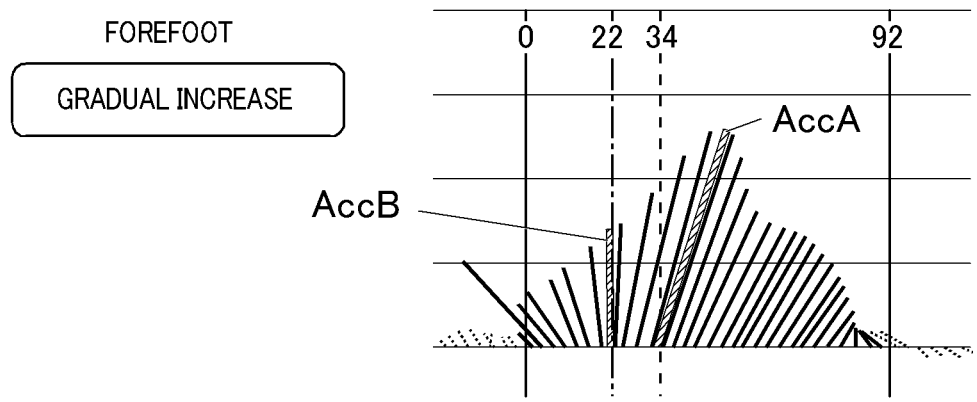
FIG. 7D is an explanatory diagram showing characteristics of a determined running method.

As shown in FIG. 7D, the gradual increase type is a running method with a shape of silhouette formed by the resultant vectors expanding rightward. The gradual increase type is classified into a forefoot running method characterized in that the foot is landed from the toe.

Figure 7E:
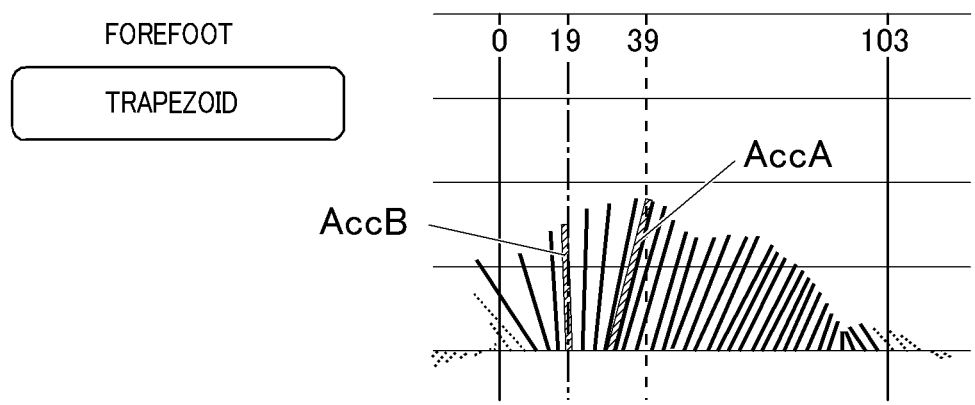
FIG. 7E is an explanatory diagram showing characteristics of a determined running method.

As shown in FIG. 7E, the trapezoid type is a running method characterized in that a shape of silhouette formed by the resultant vectors is a trapezoid. The trapezoid type is classified into a forefoot running method similarly to the gradual increase type, but may be classified into a forefoot running method with a large knee flexion.

The running method determination device 10 shows results of the above-described determination (ex. type in the section of braking, detailed classification) and/or the running method classification (heel strike/midfoot/forefoot) on the display 14.

When showing results of the above-described determination (ex. type in the section of braking, detailed classification) and/or the running method classification (heel strike/midfoot/forefoot) on the display 14, the running method determination device 10 may also show the motion analysis data showing the resultant vectors shown in FIG. 4 together so that the user can visually comprehend their type of running.

The running method determination device 10 may store the motion analysis data of first-class runners and show the motion analysis data of a first-class runner who runs by the same type of methods as the user with their motion analysis data so that the user can visually comprehend the comparison between their own running and an ideal type of running method.

The running method determination device 10 may present advice or supportive training to make the running method more appropriate or present risk of injury based on the results of the determination ((ex. type in the section of braking, detailed classification) or the running method classification (heel strike/midfoot/forefoot).

As described above, in this embodiment, the running method determination device 10 acquires the motion data during their running, and determines the running method of the user based on the concerning motion data. Specifically, the running method determination device 10 calculates the resultant vectors, the sum of the acceleration vectors in the three-axial directions, based on the acceleration data acquired from the measurement recording device 20, and determines the user's running method based on the calculated resultant vectors. Thus, as the running method determination device 10 can determine the user's running method, it is possible to make it easier for the user to comprehend the determined running method and make them correct the running method efficiently. As a result, efficient training is possible for improvement of the user's running ability.

The running method determination device 10 calculates the resultant vectors of predetermined time spans each, divides the calculated resultant vectors into multiple stages with respect to the time direction, and determines the user's running method based on the determination standard in the respective stages. It is thereby possible to determine the user's running method more objectively. Thus, the running method determination device 10 makes it possible for the user to comprehend the determined running method and correct the running method more efficiently. As a result, more efficient training is possible for improvement of the user's running ability.

As the running method determination device 10 can determine the user's running method based on the above-described motion data in each running cycle of a period since one foot touches the ground until that one foot touches the ground the next time, it is possible to determine the user's running method objectively and in detail.

The running method determination device 10 determines from which part of the user's sole the foot touches the ground when the user's sole touches the ground as the user's running method. Specifically, the running method determination device 10 determines the running method as a heel strike running method, a midfoot running method, or a forefoot running method. In the heel strike running method, the foot touches the ground from the heel. In the midfoot running method, the sole is landed in a horizontal state. In the forefoot running method, the foot touches the ground from the toe. Accordingly, as the running method determination device 10 can determine the type of landing of the user objectively, it is possible for the user to comprehend the determined type of landing and correct the type of landing efficiently. As a result, efficient training is possible for improvement of the user's running ability.

Although an embodiment of the present invention is described above, needless to say the present invention is not limited to the embodiment and can be appropriately modified in a variety of aspects without departing from the scope of the present invention.

For example, in the above-described embodiment, a running cycle of one foot (ex. left foot) in the motion analysis data is divided into two stage sections of braking and propulsion, but may be divided into multiple stage sections of foot kicking, hangtime, and the like in addition.

In the above-described embodiment, the timings of the running method determination are when the resultant vector of a specific number is calculated, when the resultant vector of the maximum brake is calculated, and when the resultant vector of the maximum propulsive acceleration, but instead of or in addition to those, the timings may also be when the foot touches the ground, when the foot leaves the ground, when the upper body sinks the most, when the acceleration vector is reversed with respect to the axial direction, when the angle of rotation of the waist is maximum, when the angle of rotation of the waist is least, and the like.

The running method determination may be targeted not only at one foot (ex. left foot) but also at both feet.

In the above-described embodiment, the running method determination device 10 determines the user's running method using the motion data of the user acquired from the measurement recording device 20, but alternatively, the running method determination device 10 may have the same as the measurement recording device 10 to measure the user's motion data itself and determine the running method when the user runs using the measured motion data.

In the above-described embodiment, the measurement recording device 20 continuously acquires the data of the accelerations in the three-axial directions (motion data) from the start to the end of running, but, for example, the measurement recording device 20 may acquire the data of the accelerations in the three-axial directions at specific points set beforehand by a user operation (ex. a point of 10 km from the start point, a point of 5 km, a point of 10 km, a point after half an hour past, a point after one hour past, a point after two hours past, and the like) at least with respect to one running cycle. The running method determination device 10 may derive the motion analysis data at each of the above-described specific points and determine the running method at the specific points based on the motion analysis data.

In the above-described embodiment, the running method determination device 10 shows the results of the running method determination on the display 14, but alternatively, the running method determination device 10 may show the results of the running method determination with the motion analysis data (see FIG. 4). In that case, the resultant vectors of the motion analysis data may be thinned out (ex. only the resultant vectors at sampling points of even number) to be shown.

In the above-described embodiment, the running method determination device 10 includes the display 14 and shows the results of the running method determination and the graph of the motion analysis data on the display 14. However, the running method determination device 10 may send the determined running method and the motion analysis data stored in the running method determination device 10 to an external device other than the running method determination device 10 and the measurement recording device 20 via the communication unit 16 and show the results of the running method determination and the graph of the motion analysis data on that external device.

Although one or more embodiments have been described, the scope of the present invention is not limited to the embodiments and includes the scope of claims below and the scope of their equivalents.

INDUSTRIAL APPLICABILITY

The present disclosure may be industrially applicable to the training support supporting improvement of the user's ability of running.

What is claimed is:

1. A running method determination device comprising:
at least one processor that executes a program stored in at least one memory,
wherein the at least one processor:
acquires motion data at a time of running of a user at a plurality of sampling points;
calculates, based on acceleration data in multiple axial directions including a front-back direction and a top-bottom direction included in motion data at each sampling point among the acquired motion data at the plurality of sampling points, a sum of acceleration vectors in the multiple axial directions as a resultant vector at said each sampling point to thereby acquire multiple resultant vectors corresponding to the plurality of sampling points
divides the calculated multiple resultant vectors into multiple stages with respect to a time direction; and
determines a type of a running method of the user using at least an angle of the multiple resultant vectors in the multiple stages as a standard of determination.

2. The running method determination device according to claim 1, wherein the at least one processor determines the type of the running method of the user using a magnitude of the multiple resultant vectors in the multiple stages as the standard of determination.

3. The running method determination device according to claim 1, wherein the standard of determination is generated based on at least an angle of the resultant vector at a specific timing in each of the multiple stages.

4. The running method determination device according to claim 3, wherein the standard of determination is generated based on a magnitude of the resultant vector at the specific timing.

5. The running method determination device according to claim 3, wherein the specific timing includes a timing when the resultant vector is calculated.

6. The running method determination device according to claim 5, wherein the specific timing further includes at least one of a timing when a foot touches a ground, a timing when the foot leaves the ground, a timing when an amount of sinking of an upper body is maximum, a timing when an acceleration vector reverses with respect to an axial direction, a timing when a rotation angle of a waist is maximum, and a timing when the rotation angle of the waist is minimum.

7. The running method determination device according to claim 1, wherein the multiple stages includes at least one of a section of braking, a section of propulsion, a section of foot kicking, and a section of hangtime with respect to the running of the user.

8. The running method determination device according to claim 3, wherein the specific timing includes a timing when the resultant vector is calculated, a timing when the resultant vector of a maximum brake in the section of braking is calculated, and a timing when the resultant vector of a maximum propulsive acceleration in the section of propulsion is calculated.

9. The running method determination device according to claim 8, wherein the specific timing further includes at least one of a timing when a foot touches a ground, a timing when the foot leaves the ground, a timing when an amount of sinking of an upper body is maximum, a timing when an acceleration vector reverses with respect to an axial direction, a timing when a rotation angle of a waist is maximum, and a timing when the rotation angle of the waist is minimum.

10. The running method determination device according to claim 1, wherein the at least one processor acquires the motion data during each period from when one foot touches a ground until the one foot touches the ground a next time at the time of the running of the user.

11. The running method determination device according to claim 1, wherein the at least one processor:
specifies a specific point at the time of the running of the user; and
determines the type of the running method of the user based on the motion data at the specified specific point.

12. The running method determination device according to claim 1, wherein the at least one processor stores the determined type of the running method of the user in at least one running method memory.

13. The running method determination device according to claim 12, wherein the at least one processor sends the type of the running methodd of the user stored in the at least one running method memory to an external device separate from the running method determination device via an antenna.

14. A running-method determination method comprising:
acquiring motion data at a time of running of a user at a plurality of sampling points;
calculating, based on acceleration data in multiple axial directions including a front-back direction and a top-bottom direction included in motion data at each sampling point among the acquired motion data at the plurality of sampling points, a sum of acceleration vectors in the multiple axial directions as a resultant vector at said each sampling point to thereby acquire multiple resultant vectors corresponding to the plurality of sampling points;
divides the calculated multiple resultant vectors into multiple stages with respect to a time direction; and
determining a type of a running method of the user using at least an angle of the multiple resultant vectors in the multiple stages as a standard of determination.

15. A non-transitory storage medium storing a running method determination program that causes a computer to:
acquire motion data at a time of running of a user at a plurality of sampling points;

calculate, based on acceleration data in multiple axial directions including a front-back direction and a top-bottom direction included in the motion data at each sampling point among the acquired motion data at the plurality of sampling points, a sum of acceleration vectors in the multiple axial directions as a resultant vector at said each sampling point to thereby acquire multiple resultant vectors corresponding to the plurality of sampling points;

divide the calculated multiple resultant vectors into multiple stages with respect to a time direction; and determine a type of a running method of the user using at least an angle of the multiple resultant vectors in the multiple stages as a standard of determination.

* * * * *

UNITED STATES PATENT AND TRADEMARK OFFICE
CERTIFICATE OF CORRECTION

| | | |
|---|---|---|
| PATENT NO. | : 12,059,594 B2 | Page 1 of 1 |
| APPLICATION NO. | : 17/442781 | |
| DATED | : August 13, 2024 | |
| INVENTOR(S) | : Nobuyoshi Nishizaka, Futoshi Yamamoto and Tsutomu Hiroyama | |

It is certified that error appears in the above-identified patent and that said Letters Patent is hereby corrected as shown below:

In the Claims

Column 9, Claim 1, Line 41, delete "points" and insert --points;--

Column 10, Claim 13, Line 43, delete "methodd" and insert --method--

Column 11, Claim 15, Line 3, after "in" delete "the"

Signed and Sealed this
First Day of October, 2024

*Katherine Kelly Vidal*

Katherine Kelly Vidal
*Director of the United States Patent and Trademark Office*